United States Patent
Yamazaki et al.

(10) Patent No.: US 8,582,124 B2
(45) Date of Patent: Nov. 12, 2013

(54) OPTICAL CHARACTERISTIC MEASURING APPARATUS AND OPTICAL CHARACTERISTIC MEASURING METHOD

(75) Inventors: Yusuke Yamazaki, Koka (JP); Sota Okamoto, Hachioji (JP)

(73) Assignee: Otsuka Electronics Co., Ltd., Hirakata-Shi (JP)

( * ) Notice: Subject to any disclaimer, the term of this patent is extended or adjusted under 35 U.S.C. 154(b) by 0 days.

(21) Appl. No.: 13/548,210

(22) Filed: Jul. 13, 2012

(65) Prior Publication Data

US 2013/0038883 A1  Feb. 14, 2013

(30) Foreign Application Priority Data

Aug. 12, 2011  (JP) ................. 2011-176817

(51) Int. Cl.
*G01B 11/28* (2006.01)
*G01B 11/06* (2006.01)

(52) U.S. Cl.
CPC ...................... *G01B 11/06* (2013.01)
USPC ....................................... 356/630

(58) Field of Classification Search
CPC ... G01B 11/06; G01N 21/211; G01N 21/9501
USPC ........................................ 356/630
See application file for complete search history.

(56) References Cited

U.S. PATENT DOCUMENTS

| | | | |
|---|---|---|---|
| 6,940,592 B2 * | 9/2005 | Borden et al. | 356/326 |
| 7,187,456 B2 * | 3/2007 | Scheiner et al. | 356/630 |
| 2003/0011786 A1 * | 1/2003 | Levy et al. | 356/600 |
| 2004/0075836 A1 | 4/2004 | Horie et al. | |
| 2010/0097607 A1 * | 4/2010 | Susaki et al. | 356/369 |
| 2013/0038883 A1 * | 2/2013 | Yamazaki et al. | 356/630 |

FOREIGN PATENT DOCUMENTS

| | | |
|---|---|---|
| JP | 2000-065536 | 3/2000 |
| JP | 2004-138519 | 5/2004 |

* cited by examiner

*Primary Examiner* — Michael P Stafira
(74) *Attorney, Agent, or Firm* — Ditthavong Mori & Steiner, P.C.

(57) ABSTRACT

An optical characteristic measuring apparatus includes a light source, a detector and a data processing unit. Data processing unit includes a modeling unit, an analyzing unit and a fitting unit. The plurality of film model equations are solved, and prescribed calculation is performed on the assumption that the optical constants included in the plurality of film model equations is identical. Fitting is performed between a waveform obtained by substituting the obtained film thickness and the obtained optical constants of the film into the film model equations and a waveform of the wavelength distribution characteristic obtained by detector, thereby determining that the optical constants included in the plurality of film model equations is identical and that the film thickness and the optical constants obtained by the analyzing unit are correct values.

6 Claims, 12 Drawing Sheets

US 8,582,124 B2

OPTICAL CHARACTERISTIC MEASURING APPARATUS AND OPTICAL CHARACTERISTIC MEASURING METHOD

BACKGROUND OF THE INVENTION

1. Field of the Invention

The present invention relates to an optical characteristic measuring apparatus and an optical characteristic measuring method, and particularly to an optical characteristic measuring apparatus and an optical characteristic measuring method capable of obtaining a film thickness and optical constants (refractive index n, extinction coefficient k) of a film formed on a substrate.

2. Description of the Background Art

When a semiconductor device or a flat panel display is manufactured, a plurality of films must be formed on a substrate. A reflection spectrometric film thickness meter disclosed in Japanese Patent Laying-Open No. 2000-65536 (PTL 1) is, for example, used to measure a film thickness and optical constants of the formed films. In the reflection spectrometric film thickness meter, light emitted from a white light source is reflected by a half mirror, and using a lens, a substrate is irradiated with the light. Furthermore, light reflected from the substrate is guided through the lens and the half mirror to a spectrometer, where the light is divided. Thereafter, a spectrum is detected by a detector that uses an image taking element such as CCD, and the detected spectrum is calculation processed. The film thickness and the optical constants of the films can thus be measured.

The film thickness and the optical constants of the formed films can also be measured using a spectroscopic ellipsometer disclosed in, for example, Japanese Patent Laying-Open No. 2004-138519 (PTL 2). In the spectroscopic ellipsometer, polarized light is emitted from a light source unit toward a substrate, and light reflected from the substrate is received by a light receiving unit to obtain a polarized spectrum of the reflected light. The film thickness and the optical constants of the formed films are thus measured.

Necessary information was, however, insufficient to obtain the only optical constants (refractive index n, extinction coefficient k) for a plurality of measuring points of the film, based only on the spectrum obtained by the spectrometric film thickness meter disclosed in PTL 1 or the spectroscopic ellipsometer disclosed in PTL 2. Therefore, the optical constants could not be obtained as the only value based on the obtained spectrum.

SUMMARY OF THE INVENTION

An object of the present invention is to provide an optical characteristic measuring apparatus and an optical characteristic measuring method capable of obtaining the only optical constants value for a plurality of measuring points of a film formed on a substrate based on an obtained spectrum.

An optical characteristic measuring apparatus according to an aspect of the present invention includes a light source, a spectrometric measuring unit, a modeling unit, an analyzing unit, and a fitting unit. The light source irradiates an object to be measured, which has at least one layer of film formed on a substrate, with measuring light having a prescribed wavelength range. The spectrometric measuring unit obtains a wavelength distribution characteristic of reflection intensity or transmission intensity based on light reflected from the object to be measured or light that has passed through the object to be measured. The modeling unit obtains a plurality of wavelength distribution characteristics from the film of a same material, and generates a plurality of film model equations including at least a parameter calculated from each of the obtained wavelength distribution characteristics as well as a film thickness and optical constants of the film. The analyzing unit solves the plurality of film model equations generated by the modeling unit, and performs prescribed calculation on the assumption that the optical constants included in the plurality of film model equations is identical, and obtains the film thickness and the optical constants of the film. The fitting unit performs fitting between a waveform obtained by substituting the film thickness and the optical constants of the film obtained by the analyzing unit into the film model equations and a waveform of the wavelength distribution characteristic obtained by the spectrometric measuring unit, thereby determining that the optical constants included in the plurality of film model equations is identical and that the film thickness and the optical constants of the film obtained by the analyzing unit are correct values.

An optical characteristic measuring method according to another aspect of the present invention includes the steps of: irradiating an object to be measured, which has at least one layer of film formed on a substrate, with measuring light having a prescribed wavelength range; obtaining a plurality of wavelength distribution characteristics of reflection intensity or transmission intensity from the film of a same material, based on light reflected from the object to be measured or light that has passed through the object to be measured; generating a plurality of film model equations including a parameter calculated from each of the obtained wavelength distribution characteristics as well as a film thickness and optical constants of the film; solving the plurality of generated film model equations, and performing prescribed calculation on the assumption that the optical constants included in the plurality of film model equations is identical, and obtaining the film thickness and the optical constants of the film; and performing fitting between a waveform obtained by substituting the obtained film thickness and the obtained optical constants of the film into the film model equations and a waveform of the obtained wavelength distribution characteristic, thereby determining that the optical constants included in the plurality of film model equations is identical and that the obtained film thickness and the obtained optical constants of the film are correct values.

According to the present invention, the only optical constants value for the plurality of measuring points of the film formed on the substrate can be obtained based on the obtained spectrum.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
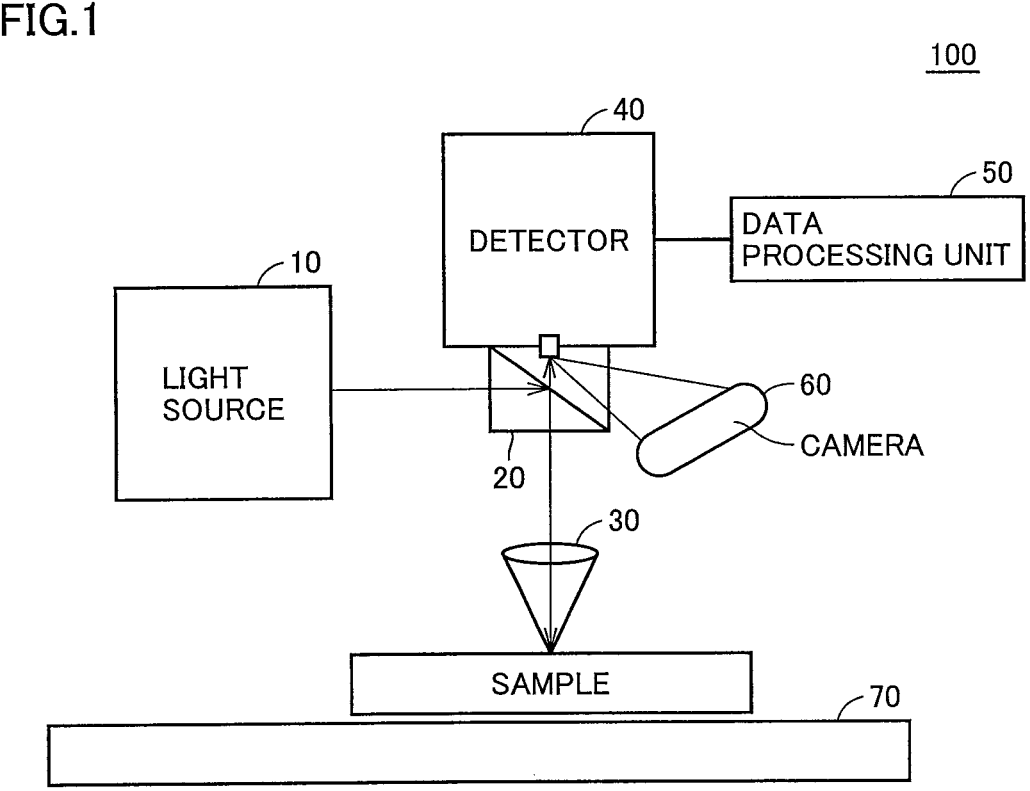
FIG. 1 is a schematic configuration diagram of an optical characteristic measuring apparatus according to a first embodiment of the present invention.

Embodiments of the present invention will be described in detail with reference to the drawings, in which the same reference characters are given to the same or corresponding portions and description thereof will not be repeated.

First Embodiment

<Apparatus Configuration>

FIG. 1 is a schematic configuration diagram of an optical characteristic measuring apparatus 100 according to a first embodiment of the present invention.

Optical characteristic measuring apparatus 100 according to the first embodiment is a microspectrometric film thickness meter and typically can measure a film thickness of each layer of a single-layer or stacked object (sample) to be measured. Optical characteristic measuring apparatus 100 according to the first embodiment is not limited to the microspectrometric film thickness meter, and may be a macrospectrometric film thickness meter. The macrospectrometric film thickness meter is not limited to a configuration that measures a reflectance, and may be a configuration that measures a reflectance by causing light from a light source to enter a sample at an angle or a configuration that measures a transmittance.

Specifically, in optical characteristic measuring apparatus 100, the sample is irradiated with light, and based on a wavelength distribution characteristic (hereinafter also referred to as "spectrum") of light reflected from the sample, a film thickness and optical constants (refractive index n, extinction coefficient k) of a film constituting the sample can be measured. Instead of the spectrum of the reflected light, a spectrum of light that has passed through the sample (spectrum of transmission light) may be used.

In the specification, a sample having at least one layer of film formed on a substrate is used as the sample by way of example. One specific example of the sample is a stacked substrate obtained by forming a resin thin film on a substrate such as an Si substrate, a glass substrate and a sapphire substrate.

Referring to FIG. 1, optical characteristic measuring apparatus 100 includes a measuring light source 10, a beam splitter 20, an objective lens 30, a detector 40, a data processing unit 50, an observation camera 60, and a stage 70. The sample is set on stage 70.

Measuring light source 10 is a light source generating measuring light having a prescribed wavelength range to obtain a reflectance spectrum of the sample. A deuterium lamp (190 nm to 450 nm) is used in the ultraviolet band, a halogen lamp (400 nm to 2000 nm) is used in the visible and near-infrared band, and a xenon lamp (300 nm to 800 nm) is used in the ultraviolet-visible band. A combined light source of the deuterium lamp and the halogen lamp that can generate ultraviolet to near-infrared wavelengths is typically used as measuring light source 10.

Beam splitter 20 reflects the measuring light generated by measuring light source 10, thereby converting the propagation direction thereof to the downward direction in the figure. Beam splitter 20 also allows light reflected from the sample and propagating in the upward direction in the figure to pass therethrough. A mask (not shown) of a reticle for focusing is provided in an optical path extending from measuring light source 10 to beam splitter 20, such that a prescribed reticle image is projected onto the sample. The reticle image is for facilitating focusing by the user even on a sample (typically a transparent glass substrate and the like) that does not have any patterns on the surface thereof. Although the reticle image may have any shapes, a concentric pattern, a cross-shaped pattern or the like can be used by way of example.

Objective lens 30 is a light focusing optical system for focusing the measuring light propagating in the downward direction in the figure. In other words, objective lens 30 converges the measuring light such that an image is formed on the sample or at a position near the sample. Objective lens 30 is also a magnifying lens having a prescribed magnification (e.g., 10×, 20×, 30×, 40× or the like), and can make a region where the optical characteristic of the sample is measured smaller than a beam cross section of the light entering objective lens 30.

The measuring light and observation light that have entered the sample from objective lens 30 are reflected from the sample and propagate in the upward direction in the figure. This reflected light passes through objective lens 30 and beam splitter 20, and reaches detector 40.

Detector 40 is a spectrometric measuring instrument, and measures a reflectance spectrum based on the reflected light that has passed through beam splitter 20 and outputs the measurement result to data processing unit 50. More specifically, detector 40 includes a slit, a diffraction grating, a detection element, a cut filter, and a shutter, although they are not shown.

The slit, the cut filter, the shutter, and the diffraction grating are arranged on an optical axis of the reflected light. The slit is used to restrict an area of the reflected light passing through beam splitter 20 and entering detector 40. By using the slit, the area of the reflected light entering the diffraction grating is restricted and the accuracy of breaking down the light into respective wavelength components can be increased. The cut filter is an optical filter for restricting wavelength components outside the measuring range included in the reflected light passing through beam splitter 20 and entering detector 40, and particularly blocks the wavelength components outside the measuring range. The shutter is used to block light entering the detection element, at the time of resetting the detection element, for example. The shutter is typically a mechanical shutter driven by electromagnetic force.

The diffraction grating divides the incident reflected light and guides the respective divided light waves to the detection element. Specifically, the diffraction grating is a reflection-type diffraction grating and is configured such that diffracted waves at every prescribed wavelength intervals are reflected in the corresponding directions. When the reflected wave enters the diffraction grating having such a configuration, the respective wavelength components included therein are reflected in the corresponding directions and enter a prescribed detection region of the detection element. This wavelength interval corresponds to the wavelength resolution in detector 40. The diffraction grating is typically a flat-focus-type spherical grating.

In order to measure the reflectance spectrum of the sample, the detection element outputs an electrical signal corresponding to the light intensity of the respective wavelength components included in the reflected light divided by the diffraction grating. The detection element is a photodiode array and the like having a sensitivity to the ultraviolet-visible region.

Data processing unit 50 performs the characteristic processing according to the present invention on the reflectance spectrum obtained by detector 40, thereby measuring the film thickness and the optical constants of the film constituting the sample. Details of the processing by data processing unit 50 will be described below. Data processing unit 50 then outputs the optical characteristic including the measured film thickness of the film constituting the sample.

A part of the reflected light that has passed through beam splitter 20 enters observation camera 60. Observation camera 60 is an image taking unit obtaining a reflection image obtained by the reflected light, and is typically formed of a CCD (Charged Coupled Device) sensor, a CMOS (Complementary Metal Oxide Semiconductor) sensor or the like. Observation camera 60 is typically a camera having a sensitivity to the visible band, and in many cases, observation camera 60 has a sensitivity characteristic different from that of detector 40 having a sensitivity to the prescribed measuring range. Observation camera 60 then outputs, to a display unit (not shown), a video signal corresponding to the reflection image obtained by the reflected light. The display unit displays the reflection image on a screen based on the video signal provided from observation camera 60. The user sees this reflection image displayed on the display unit, and performs focusing on the sample or checks a measuring position. The display unit is typically a liquid crystal display (LCD) or the like. Instead of observation camera 60 and the display unit, a finder through which the user can directly see the reflection image may be provided.

Stage 70 is a sample platform on which the sample is arranged, and an arrangement plane thereof is formed to be flat. This stage 70 is freely driven in three directions (X direction, Y direction and Z direction) by a mechanically-coupled movable mechanism (not shown) as one example. The movable mechanism is typically configured to include servo motors for three axes and servo drivers for driving the respective servo motors. The movable mechanism drives stage 70 in response to a stage position command provided from the user, a not-shown control apparatus or the like. Stage 70 is driven as described above, so that a positional relationship between the sample and objective lens 30 described below is changed.

<Configuration of Data Processing Unit>

Figure 2:
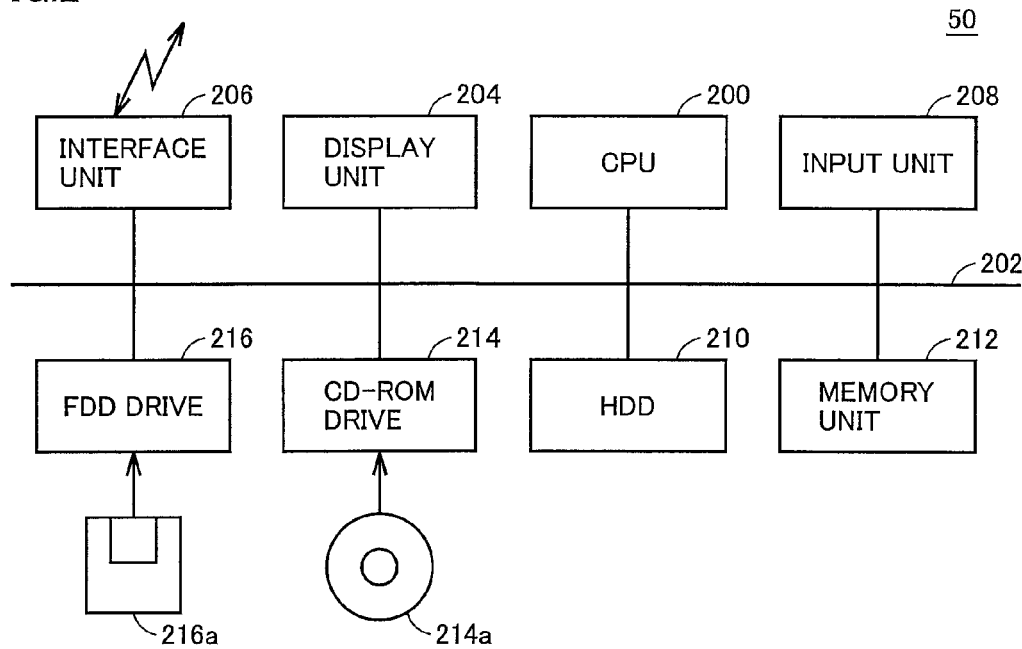
FIG. 2 is a schematic view showing a hardware configuration of an overview of a data processing unit according to the first embodiment of the present invention.

FIG. 2 is a schematic view showing a hardware configuration of an overview of data processing unit 50 according to the first embodiment of the present invention.

Referring to FIG. 2, data processing unit 50 includes a CPU (Central Processing Unit) 200 implemented typically by a computer and executing various types of programs including the Operating System (OS), a memory unit 212 temporarily storing data necessary for execution of the programs by CPU 200, and a hard disk drive (HDD) 210 storing the programs executed by CPU 200 in a non-volatile manner. A program for implementing the processing described below is prestored in hard disk drive 210, and this program is read by a flexible disk drive (FDD) 216 or a CD-ROM drive 214 from a flexible disk 216a, a CD-ROM (Compact Disk-Read Only Memory) 214a or the like, respectively.

CPU 200 receives an instruction from the user and the like through an input unit 208 constituted by a keyboard, a mouse and the like, and outputs, to a display unit 204, a measurement result and the like measured by execution of the programs. The respective units are connected to one another by a bus 202.

<Calculation Processing Structure>

Description will be given to calculation processing executed by data processing unit 50 according to the first embodiment on the reflectance spectrum obtained by detector 40 in order to measure the film thickness and the optical constants of the film constituting the sample.

Figure 3:
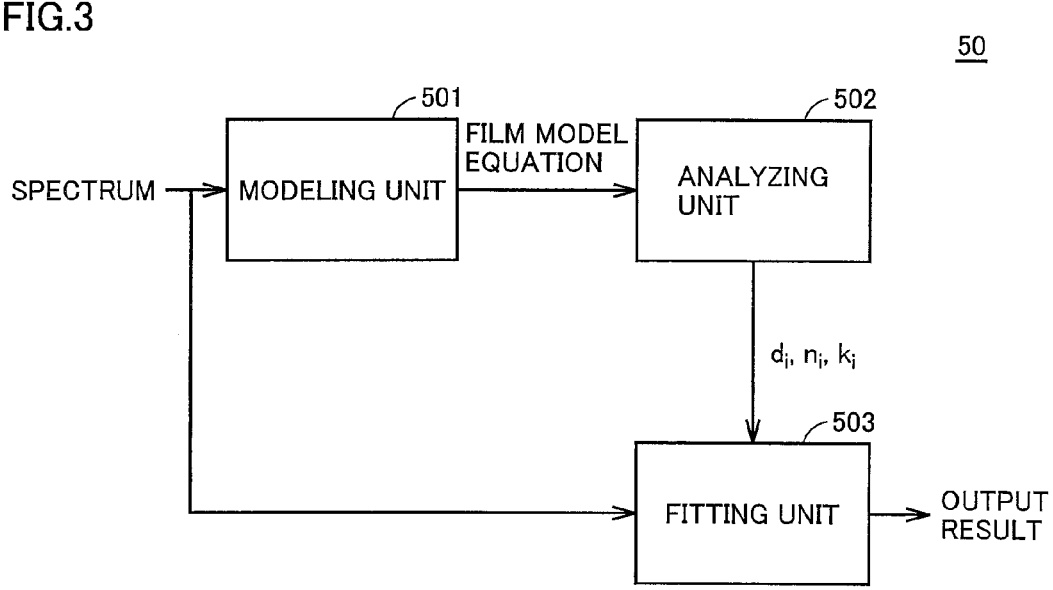
FIG. 3 is a block diagram showing a calculation processing structure of the data processing unit according to the first embodiment of the present invention.

FIG. 3 is a block diagram showing a calculation processing structure of data processing unit 50 according to the first embodiment of the present invention. The block diagram shown in FIG. 3 is implemented by CPU 200 reading out the program prestored in hard disk drive 210 and the like into memory unit 212 and the like and executing the program.

Referring to FIG. 3, data processing unit 50 (FIG. 1) includes, as its functions, a modeling unit 501, an analyzing unit 502 and a fitting unit 503.

Modeling unit 501 calculates a parameter relating to the sample from an actually measured reflectance spectrum $R(\lambda)$ outputted from detector 40 (FIG. 1), and determines a film model equation (function) of the sample based on the calculated parameter.

<Principle of Calculation Processing>

Before describing the film model equation, mathematical and physical studies will be first conducted on the reflected light observed when the sample is irradiated with the measuring light.

Figure 4:
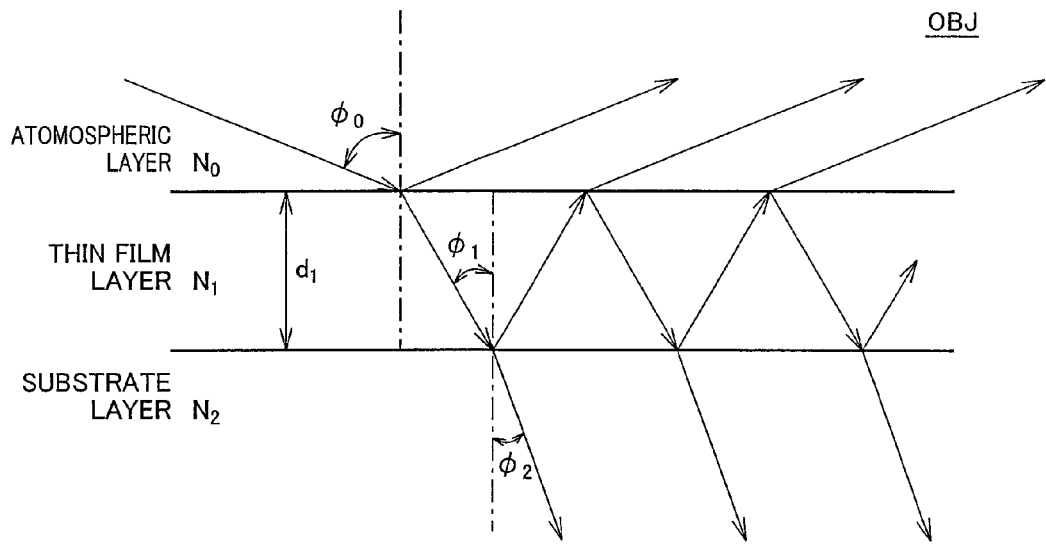
FIG. 4 is one example of a schematic cross-sectional view of a sample to be measured by the optical characteristic measuring apparatus according to the first embodiment of the present invention.

FIG. 4 is one example of a schematic cross-sectional view of a sample to be measured by optical characteristic measuring apparatus 100 according to the first embodiment of the present invention.

Referring to FIG. 4, a sample OBJ has a two-layer structure including a substrate layer and a thin film layer formed on the substrate layer. The irradiation light provided from optical characteristic measuring apparatus 100 enters sample OBJ from the upper side in the figure. In other words, the measuring light first enters the thin film layer.

In order to facilitate understanding, reflected light generated when the measuring light that has entered sample OBJ is reflected from an interface between the substrate layer and the thin film layer will be discussed. In the description below, each layer is expressed using a subscript "i". Specifically, a subscript "0" is used for an atmospheric layer such as air and vacuum, a subscript "1" is used for the thin film layer of sample OBJ, and a subscript "2" is used for the substrate layer. Using the subscript "i", a complex refractive index N, a film thickness d and an incidence angle $\phi$ in each layer are expressed as a complex refractive index $N_i$, a film thickness $d_i$ and an incidence angle $\phi_i$, respectively.

When light enters the thin film layer shown in FIG. 4 at an incidence angle $\phi_0$, the incident light is reflected from an interface between the atmospheric layer and the thin film layer as well as from the interface between the thin film layer and the substrate layer, which have different refractive indexes, and the light is reflected many times in the thin film layer, which results in interference. Therefore, a reflectance, a transmittance, a phase difference $\Delta$, and an amplitude ratio $\Psi$ of the thin film layer shown in FIG. 4 are expressed like equation (1):

$$\text{reflectance} = (|R_p|^2 + |R_s|^2)/2 \quad \text{equation (1)}$$

$$\text{transmittance} =$$
$$\left(\frac{Re(n_2\cos\phi_2)}{Re(n_0\cos\phi_0)} \times |T_p|^2 + \frac{Re(n_2/\cos\phi_2)}{Re(n_0/\cos\phi_0)} \times |T_s|^2\right)/2$$

$$\tan\Psi e^{j\Delta} = \frac{R_p}{R_s}.$$

In this equation, $R_p$ represents a complex reflection coefficient of a P component of the polarized light, $R_s$ represents a complex reflection coefficient of an S component of the polarized light, $T_p$ represents a complex transmission coefficient of the P component of the polarized light, and $T_s$ represents a complex transmission coefficient of the S component of the polarized light.

These complex reflection coefficients $R_p$ and $R_s$ as well as complex transmission coefficients $T_p$ and $T_s$ can be obtained by calculation below. First, using a refractive index and an extinction coefficient complex refractive index $N_i$ can be expressed like equation (2):

$$N_i = n_i - jk_i \quad \text{equation (2)}.$$

Reflection and transmission of the light occur at the interfaces having different refractive indexes. An amplitude reflectance (Fresnel coefficient) of the P component and an amplitude reflectance of the S component of the polarized light at an interface between an i layer and an i+1 layer, which have different refractive indexes, are expressed like equation (3):

$$r_{i,i+1p} = \frac{N_{i+1}\cos\phi_i - N_i\cos\phi_{i+1}}{N_{i+1}\cos\phi_i + N_i\cos\phi_{i+1}}, \quad \text{equation (3)}$$

$$r_{i,i+1s} = \frac{N_i\cos\phi_i - N_{i+1}\cos\phi_{i+1}}{N_i\cos\phi_i + N_{i+1}\cos\phi_{i+1}}.$$

Similarly, an amplitude transmittance (Fresnel coefficient) of the P component and an amplitude transmittance of the S component of the polarized light are expressed like equation (4):

$$t_{i,i+1p} = \frac{2N_i\cos\phi_i}{N_{i+1}\cos\phi_i + N_i\cos\phi_{i+1}}, \quad \text{equation (4)}$$

$$t_{i,i+1s} = \frac{2N_i\cos\phi_i}{N_i\cos\phi_i + N_{i+1}\cos\phi_{i+1}}.$$

Incidence angle $\phi_i$ can be calculated from an incidence angle at the uppermost atmospheric layer (0 layer) in accordance with the Snell's law ($N_0 \sin\phi_0 = N_i \sin\phi_i$) described below.

Light reflected at the reflectance expressed by equation (3) is reflected many times in a layer having a film thickness that allows interference of the light. Therefore, since the light directly reflected from the interface between the adjacent layers is different in optical path length from the light multiply-reflected in the layer, they become different in phase from each other, which causes interference of the light. In order to describe the interference effect of the light in each layer, a phase angle $\beta_i$ of the light in the i layer is introduced. Then, phase angle $\beta_i$ can be expressed like equation (5):

$$\beta_i = 2\pi\left(\frac{d_i}{\lambda}\right)N_i\cos\phi_i. \quad \text{equation (5)}$$

In this equation, $d_i$ represents a film thickness of the i layer and $\lambda$ represents a wavelength of the incident light.

Using equations (2) to (5), complex reflection coefficient $R_p$ of the P component and complex reflection coefficient $R_s$ of the S component of the polarized light in sample OBJ formed of three layers, i.e., the atmospheric layer, the thin film layer and the substrate layer can be expressed by equation (6):

$$R_p = \frac{r_{01p} + \gamma \times r_{12p}e^{-j2\beta_1}}{1 + \gamma \times r_{01p}r_{12p}e^{-j2\beta_1}}, \quad \text{equation (6)}$$

$$R_s = \frac{r_{01s} + \gamma \times r_{12s}e^{-j2\beta_1}}{1 + \gamma \times r_{01s}r_{12s}e^{-j2\beta_1}}.$$

In this equation, $\gamma$ represents a rear surface reflection coefficient contribution ratio, which is a ratio of light reflected from the rear surface side of a thick layer like the substrate layer. When the rear surface reflection coefficient contribution ratio is omitted, $\gamma$ may only be set to 1.

Similarly, complex transmission coefficient $T_p$ of the P component and complex transmission coefficient $T_s$ of the S component can be expressed by equation (7):

$$T_p = \frac{t_{01p}t_{12p}e^{-j\beta_1}}{1 + r_{01p}r_{12p}e^{-j2\beta_1}}, \quad \text{equation (7)}$$

$$T_s = \frac{t_{01s}t_{12s}e^{-j\beta_1}}{1 + r_{01s}r_{12s}e^{-j2\beta_1}}.$$

By substituting equations (6) and (7) into equation (1), the reflectance, the transmittance, phase difference $\Delta$, and amplitude ratio $\Psi$ can be expressed as the film model equations.

As described above, the film model equation is a relational equation expressing the reflectance, the transmittance, phase difference $\Delta$, amplitude ratio $\Psi$ and the like using aforementioned incidence angle $\phi_i$, wavelength $\lambda$ of the incident light, complex refractive index $N_i$, film thickness $d_i$, and rear surface reflection coefficient contribution ratio $\gamma$.

Furthermore, film model equations such as the Cauchy model, the Forouhi-Bloomer model, the EMA model, the Lorentz model, the Tauc-Lorentz model, and the Drude model are known with regard to the optical constants (refractive index $n_i$, extinction coefficient $k_i$) of the film calculated by optical characteristic measuring apparatus 100.

Specifically, the film model equation expressing the optical constants by the Cauchy model can be expressed like equation (8):

$$n_i = \frac{C_3}{\lambda^4} + \frac{C_2}{\lambda^2} + C_1 \quad \text{equation (8)}$$

$$k_i = 0.$$

In this equation, $C_1$, $C_2$ and $C_3$ are variables of the film model equation.

The film model equation expressing the optical constants by the Forouhi-Bloomer model can be expressed like equation (9):

$$k_i = C_1(E-C_4)^2/(E^2 - C_2E + C_3)$$

$$E = hc/\lambda$$

$$n_i = C_5 + g(E) \quad \text{equation (9).}$$

In this equation, h represents a Planck's constant, c represents a speed of light in vacuum, g(E) represents an integral value of $k_i$, and $C_1$, $C_2$, $C_3$, $C_4$, and $C_5$ are variables of the film model equation. An equation for obtaining $n_i$ is derived from an equation for obtaining $k_i$ by integration with a Kramers-Kronig relational equation expressed by equation (10):

$$n(\omega) = 1 + \frac{2}{\pi} P \int_0^\infty \frac{\omega' k(\omega')}{\omega'^2 - \omega^2} d\omega' \quad \text{equation (10)}$$

$$k(\omega) = -\frac{2}{\pi} P \int_0^\infty \frac{n(\omega')}{\omega'^2 - \omega^2} d\omega'.$$

In this equation, P represents a principal value of Cauchy integral, and w represents a frequency.

Referring to FIG. 3 again, modeling unit 501 generates film model equations for respective measuring points, based on spectra obtained for the respective measuring points. For example, when measurement is conducted at five points in one substrate or when measurement is conducted at one point in each of five substrates, modeling unit 501 generates five film model equations for the respective measuring points, based on five spectra obtained for the respective measuring points.

Next, analyzing unit 502 solves the plurality of film model equations generated by modeling unit 501, and performs calculation in accordance with the non-linear least square method on the assumption that optical constants n and k included in the plurality of film model equations are identical, and obtains film thickness $d_i$ and optical constants n and k of the film. The non-linear least square method is described by way of example, and other calculation methods may be used as long as they can obtain film thickness $d_i$ and optical constants n and k of the film.

The non-linear least square method is a method for calculating a parameter (film thickness $d_i$ and optical constants $n_i$ and $k_i$ of the film) that achieves a minimum square sum of a residual $\Delta Y$ between measured spectral data Ym and spectral data Yc calculated from the film model equations. In the actual calculation, an amount of change in the parameter can be obtained by solving a determinant as expressed by equation (11):

$$Y = XP$$

$$X^T Y = X^T X P$$

$$(X^T X)^{-1} X^T Y = P \quad \text{equation (11)}$$

where Y represents a residual matrix, X represents a partial differential matrix, and P represents a parameter change amount matrix.

Conventionally, the determinant used in the non-linear least square method was created like equation (12) for each of the generated film model equations, and the calculation was performed.

$$\begin{bmatrix} \Delta Y_1 \\ \vdots \\ \Delta Y_n \end{bmatrix} = \begin{bmatrix} \frac{\partial f_1}{\partial C_1} & \frac{\partial f_1}{\partial C_2} & \frac{\partial f_1}{\partial C_3} & \frac{\partial f_1}{\partial d} \\ \vdots & \vdots & \vdots & \vdots \\ \frac{\partial f_n}{\partial C_1} & \frac{\partial f_n}{\partial C_2} & \frac{\partial f_n}{\partial C_3} & \frac{\partial f_n}{\partial d} \end{bmatrix} \begin{bmatrix} \Delta C_1 \\ \Delta C_2 \\ \Delta C_3 \\ \Delta d \end{bmatrix} \quad \text{equation (12)}$$

$$\Delta Y_y = Ym_y - Yc_y$$

$$Yc_y = f_y(\phi, \lambda_y, N_0, N_1, d_1, \ldots, N_i, d_i, \gamma)(y = 1 \sim n)$$

Since the Cauchy model is used in equation (12), optical constants $n_i$ and $k_i$ are expressed as variables of $C_1$, $C_2$ and $C_3$.

However, since analyzing unit 502 solves the plurality of film model equations generated by modeling unit 501, the determinant used in the non-linear least square method is created like equation (13) obtained by synthesizing the plurality of film model equations, and the calculation is performed.

$$\begin{bmatrix} \Delta Y_{11} \\ \vdots \\ \Delta Y_{1n} \\ \vdots \\ \Delta Y_{m1} \\ \vdots \\ \Delta Y_{mn} \end{bmatrix} = \begin{bmatrix} \frac{\partial f_{11}}{\partial C_1} & \frac{\partial f_{11}}{\partial C_2} & \frac{\partial f_{11}}{\partial C_3} & \frac{\partial f_{11}}{\partial d_1} & \frac{\partial f_{11}}{\partial d_2} & \cdots & \frac{\partial f_{11}}{\partial d_m} \\ \vdots & \vdots & \vdots & \vdots & \vdots & \ddots & \vdots \\ \frac{\partial f_{1n}}{\partial C_1} & \frac{\partial f_{1n}}{\partial C_2} & \frac{\partial f_{1n}}{\partial C_3} & \frac{\partial f_{1n}}{\partial d_1} & \frac{\partial f_{1n}}{\partial d_2} & \cdots & \frac{\partial f_{1n}}{\partial d_m} \\ \vdots & \vdots & \vdots & \vdots & \vdots & \ddots & \vdots \\ \frac{\partial f_{m1}}{\partial C_1} & \frac{\partial f_{m1}}{\partial C_2} & \frac{\partial f_{m1}}{\partial C_3} & \frac{\partial f_{m1}}{\partial d_1} & \frac{\partial f_{m1}}{\partial d_2} & \cdots & \frac{\partial f_{m1}}{\partial d_m} \\ \vdots & \vdots & \vdots & \vdots & \vdots & \ddots & \vdots \\ \frac{\partial f_{mn}}{\partial C_1} & \frac{\partial f_{mn}}{\partial C_2} & \frac{\partial f_{mn}}{\partial C_3} & \frac{\partial f_{mn}}{\partial d_1} & \frac{\partial f_{mn}}{\partial d_2} & \cdots & \frac{\partial f_{mn}}{\partial d_m} \end{bmatrix} \quad \text{equation (13)}$$

$$\begin{bmatrix} \Delta C_1 \\ \Delta C_2 \\ \Delta C_3 \\ \Delta d_1 \\ \Delta d_2 \\ \vdots \\ \Delta d_m \end{bmatrix}$$

$$\Delta Y_{xy} = Ym_{xy} - Yc_{xy}$$

$$Yc_{xy} = f_{xy}(\phi, \lambda_y, N_{x0}, N_{x1}, d_{x1}, \ldots, N_{xi}, d_{xi}, \gamma)$$

$$(x = 1 \sim m, y, = 1 \sim n)$$

Since the Cauchy model is used in equation (13) as well, optical constants $n_i$ and $k_i$ are expressed as variables of $C_1$, $C_2$ and $C_3$. In equation (13), a partial differential parameter does not exist in a film model equation f, and thus, the term of the partial differential parameter (e.g., the term partially differentiating $f_{11}$ by $d_2$) is zero.

Furthermore, analyzing unit 502 solves equation (13) on the assumption that optical constants n and k are identical. In other words, it is assumed that variables $C_1$, $C_2$ and $C_3$ have a relationship expressed by equation (14):

$$C_1 = C_{11} = C_{12} = \ldots = C_{1m}$$

$$C_2 = C_{21} = C_{22} = \ldots = C_{2m}$$

$$C_3 = C_{31} = C_{32} = \ldots = C_{3m} \qquad \text{equation (14)}.$$

As a result, analyzing unit 502 can solve the determinant of equation (13), and obtains the amount of change in the parameter and obtains film thickness $d_i$ and optical constants $n_i$ and $k_i$ of the film.

Figure 5A:
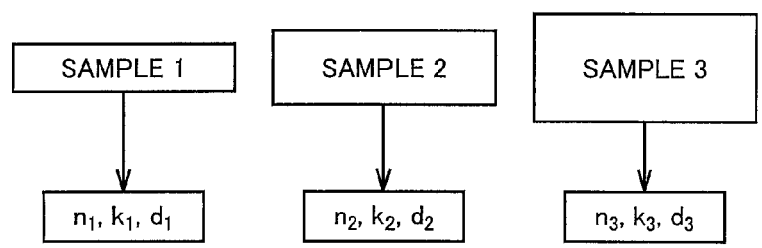
FIGS. 5A and 5B schematically show a relationship between the sample and a film thickness $d_i$ and optical constants $n_i$ and $k_i$ of a film.
Figure 5B:
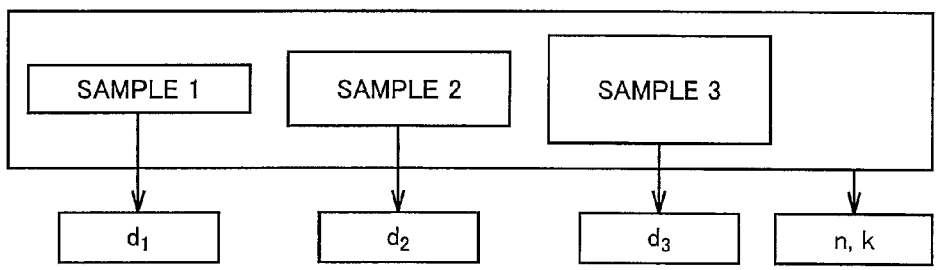

FIGS. 5A and 5B schematically show a relationship between the sample and film thickness $d_i$ and optical constants $n_i$ and $k_i$ of the film. In FIG. 5A, film model equations were generated for a sample 1, a sample 2 and a sample 3, respectively, on which a film of the same material is formed, and film thickness $d_i$ and optical constants $n_i$ and $k_i$ of the film were obtained using the non-linear least square method. Therefore, different values of optical constants $n_i$ and $k_i$ of the film were obtained for sample 1, sample 2 and sample 3, and optical constants $n_i$ and $k_i$ of the film could not be obtained as the only values.

In the method according to the present invention, as shown in FIG. 5B, film thickness $d_i$ and optical constants n and k of the film are collectively obtained using the non-linear least square method for sample 1, sample 2 and sample 3 each having the film of the same material formed thereon, assuming that optical constants n and k of the film are identical. Therefore, optical constants n and k of the film of the same material can be obtained as the only values.

Referring to FIG. 3 again, fitting unit 503 performs fitting between a waveform obtained by substituting film thickness $d_i$ and optical constants n and k of the film obtained by analyzing unit 502 into the film model equations and a waveform of the spectrum obtained by detector 40 (FIG. 1). By performing fitting between both waveforms, fitting unit 503 can determine that optical constants n and k included in the plurality of film model equations are identical and that obtained film thickness $d_i$ and optical constants n and k of the film are correct values.

On the other hand, if the waveform obtained by substituting film thickness $d_i$ and optical constants n and k of the film obtained by analyzing unit 502 into the film model equations does not fit the waveform of the obtained spectrum, fitting unit 503 can determine that optical constants n and k of the film are not identical or that the film model equations themselves are different.

In other words, fitting unit 503 verifies whether or not optical constants n and k of the film are identical and whether or not the film model equations are correct. As a result, the accuracy of film thickness $d_i$ and optical constants n and k of the film obtained by analyzing unit 502 can be increased.

<Measuring Method>

Next, an optical characteristic measuring method according to the first embodiment of the present invention will be described with reference to a flowchart.

Figure 6:
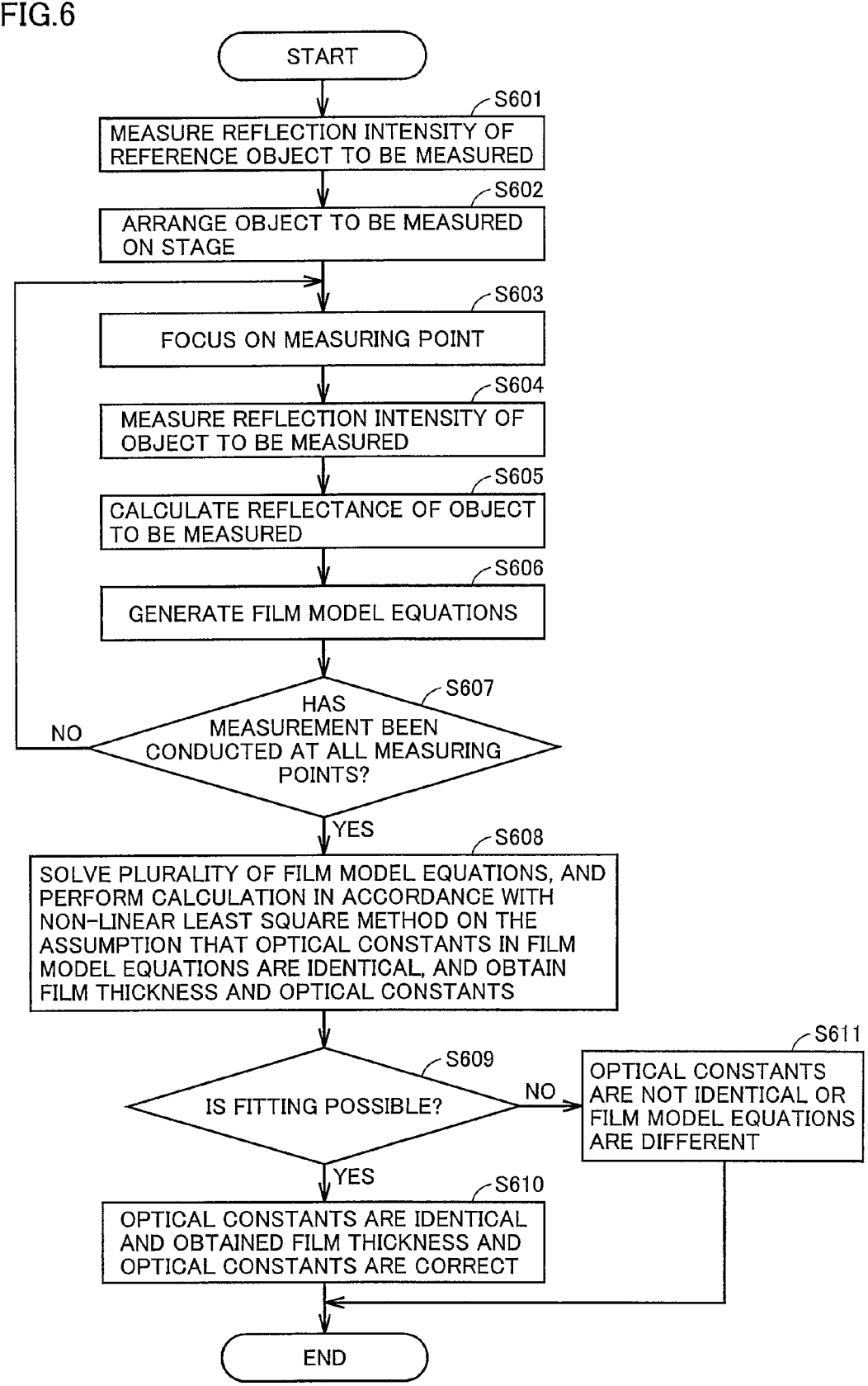
FIG. 6 is a flowchart showing a process procedure of an optical characteristic measuring method according to the first embodiment of the present invention.

FIG. 6 is a flowchart showing a process procedure of the optical characteristic measuring method according to the first embodiment of the present invention.

Referring to FIG. 6, before measuring a sample, which is an object to be measured, optical characteristic measuring apparatus 100 first measures reflection intensity of a reference object to be measured that has known optical constants of a film (step S601). Then, the user arranges the object to be measured (sample) on stage 70 (FIG. 1) (step S602).

Then, the user moves objective lens 30 and stage 70 to focus on a measuring point, while referring to a reflection image taken by observation camera 60 (FIG. 1) and displayed on the display unit (not shown) (step S603).

When the user provides a measurement start command after focusing on the measuring point, generation of measuring light from measuring light source 10 (FIG. 1) starts. Detector 40 receives light reflected from the sample, and outputs a reflection intensity spectrum based on the reflected light to data processing unit 50 (reflection intensity measurement) (step S604). Then, CPU 200 in data processing unit 50 temporarily stores the reflection intensity spectrum detected by detector 40 in memory unit 212 and the like, and thereafter, calculates a reflectance of the sample based on the reflection intensity spectrum (step S605).

CPU 200 generates film model equations including at least the calculated reflectance of the sample as well as a film thickness and optical constants of the film (step S606). Then, CPU 200 determines whether or not measurement has been conducted at all measuring points (step S607). If CPU 200 determines that measurement has not yet been conducted at all measuring points (NO in step S607), the user moves objective lens 30 and stage 70 to focus on the next measuring point, while referring to the reflection image taken by observation camera 60 (FIG. 1) and displayed on the display unit (not shown) (step S603).

If CPU 200 determines that measurement has been conducted at all measuring points (YES in step S607), the process proceeds to step S608. CPU 200 solves the plurality of film model equations, and performs calculation in accordance with the non-linear least square method on the assumption that the optical constants included in the plurality of film model equations are identical, and obtains film thickness $d_i$ and optical constants n and k of the film (step S608).

Furthermore, CPU 200 performs fitting between a waveform obtained by substituting obtained film thickness $d_i$ and optical constants n and k of the film into the film model equations and a waveform of the spectrum obtained by detector 40, and determines whether or not fitting is possible (step S609). If CPU 200 determines that fitting is possible (YES in step S609), CPU 200 determines that optical constants n and k included in the plurality of film model equations are identical and that obtained film thickness $d_i$ and optical constants n and k of the film are correct (step S610). If CPU 200 determines that fitting is impossible (NO in step S609), CPU 200 determines that optical constants n and k included in the plurality of film model equations are not identical or that the generated film model equations are different (step S611).

Figures 7A, 7B, 7C:
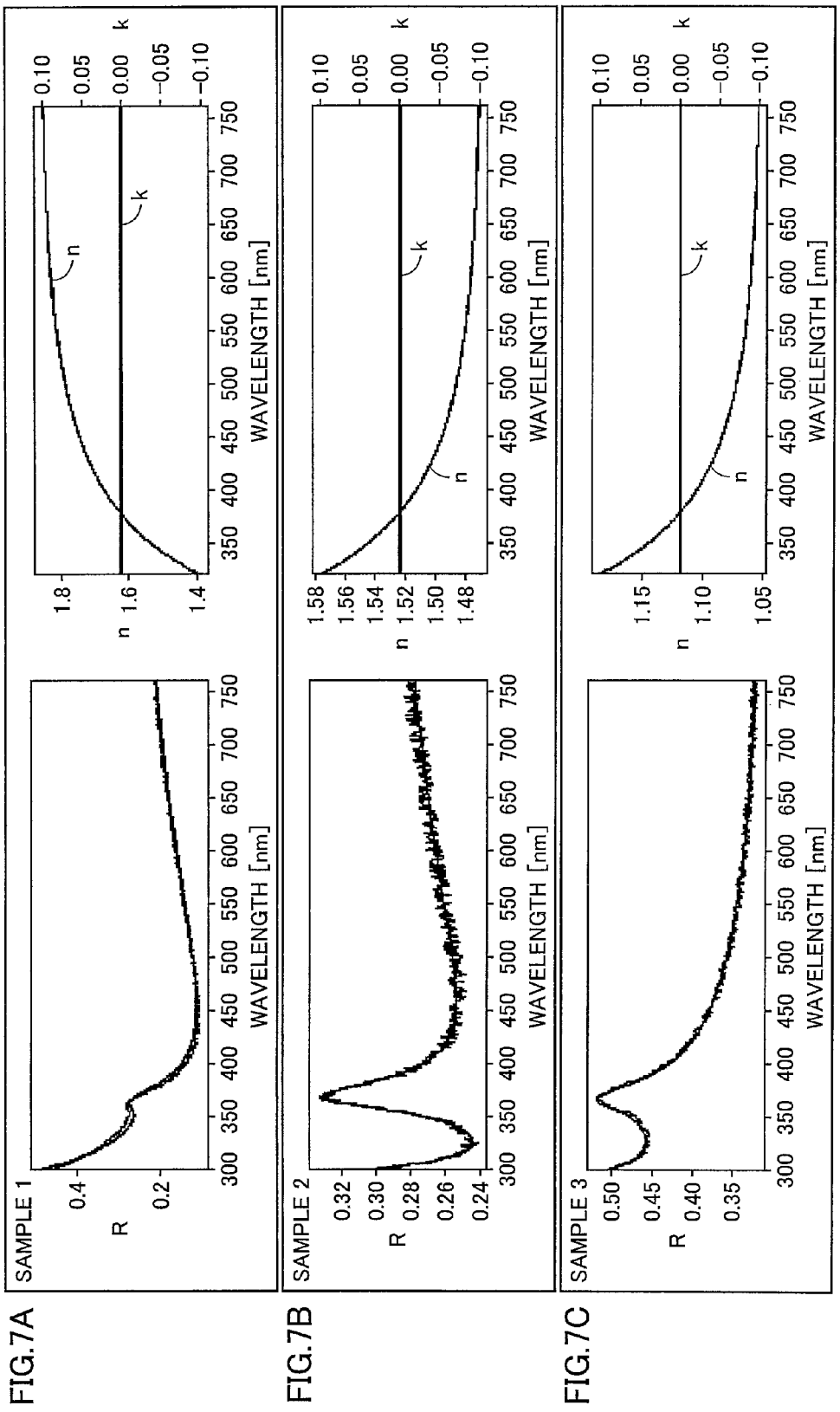
FIGS. 7A to 7C are graphs showing results obtained by measuring samples using a conventional optical characteristic measuring apparatus.

Next, description will be given to results obtained by measuring (simulating) the sample using optical characteristic measuring apparatus 100. First, FIGS. 7A to 7C are graphs showing results obtained by measuring samples using a conventional optical characteristic measuring apparatus. FIG. 7A shows a graph of a reflectance spectrum of sample 1 and a graph of optical constants n and k of the film of sample 1. FIG. 7B shows a graph of a reflectance spectrum of sample 2 and a graph of optical constants n and k of the film of sample 2. FIG. 7C shows a graph of a reflectance spectrum of sample 3 and a graph of optical constants n and k of the film of sample 3. In the graphs of the reflectance spectrum, the horizontal axis indicates a wavelength and the vertical axis indicates a reflectance. In the graphs of optical constants n and k of the film, the horizontal axis indicates a wavelength, and the vertical axis on the left indicates a refractive index and the vertical axis on the right indicates an extinction coefficient. Sample 1 to sample 3 are obtained by forming resin films of different film thicknesses on Si substrates, respectively.

As shown in FIGS. 7A to 7C, extinction coefficient k remains unchanged and remains at the same value in sample 1 to sample 3, whereas sample 1 is different in refractive index n from samples 2 and 3, and thus, optical constants n and k of the resin film cannot be obtained as the only values. The film thickness of the resin film of sample 1 is calculated as 49.1 nm. The film thickness of the resin film of sample 2 is calculated as 45.6 nm. The film thickness of the resin film of sample 3 is calculated as 65.4 nm.

As shown in FIGS. 7A to 7C, the conventional optical characteristic measuring apparatus had such a problem that different optical constants n and k are obtained, although obtained optical constants n and k should be identical because the same resin film is used.

Figure 8A:
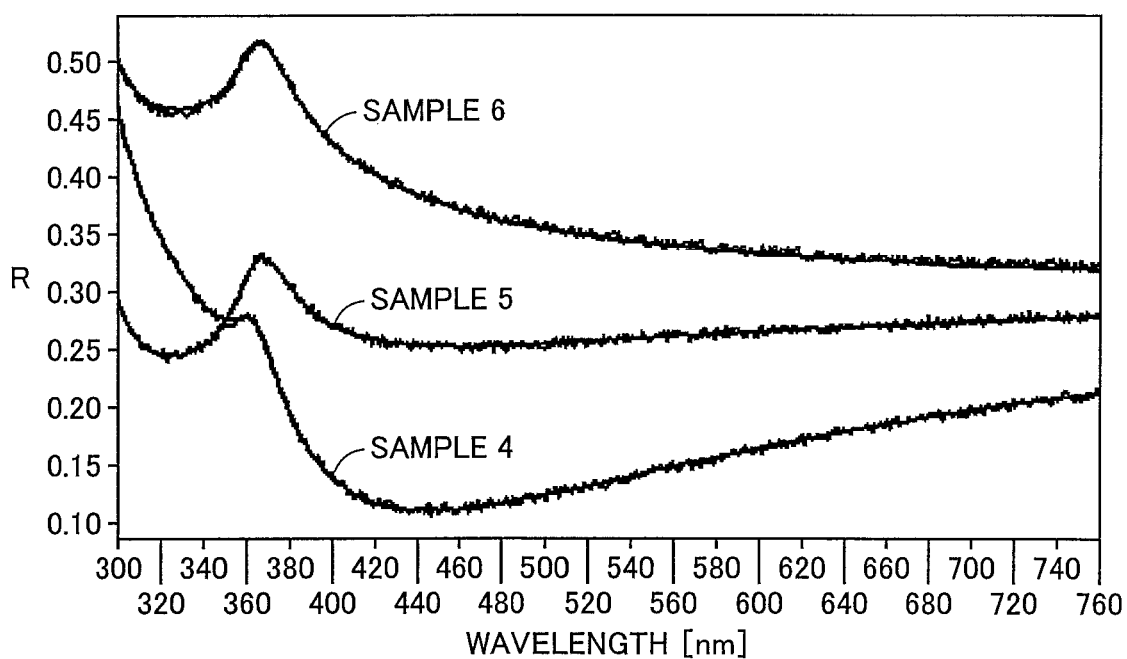
FIGS. 8A and 8B are graphs showing results obtained by measuring samples using the optical characteristic measuring apparatus according to the first embodiment of the present invention.
Figure 8B:
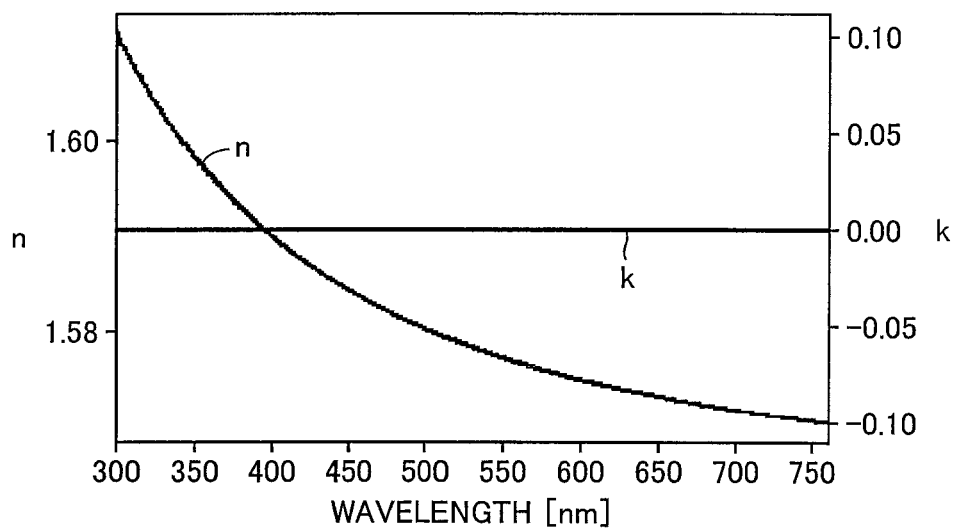

FIGS. 8A and 8B are graphs showing results obtained by measuring samples using optical characteristic measuring apparatus 100 according to the first embodiment of the present invention. FIG. 8A shows a graph of reflectance spectra of a sample 4 to a sample 6. FIG. 8B shows a graph of optical constants n and k of the films of sample 4 to sample 6. In the graph of the reflectance spectra, the horizontal axis indicates a wavelength and the vertical axis indicates a reflectance. In the graph of optical constants n and k of the films, the horizontal axis indicates a wavelength, and the vertical axis on the left indicates a refractive index and the vertical axis on the right indicates an extinction coefficient. Sample 4 to sample 6 are obtained by forming resin films of different film thicknesses on Si substrates, respectively.

As shown in FIGS. 8A and 8B, optical constants n and k remain unchanged in sample 4 to sample 6 and can be obtained as the only values representing the optical constants of the resin film. The film thickness of the resin film of sample 4 is calculated as 60.8 nm. The film thickness of the resin film of sample 5 is calculated as 40.8 nm. The film thickness of the resin film of sample 6 is calculated as 19.8 nm.

Figure 9A:
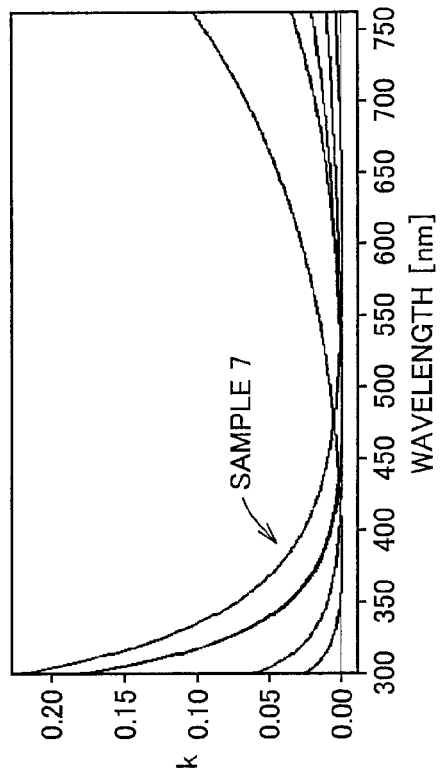
FIGS. 9A to 9D are graphs showing results obtained by measuring a sample having different optical constants n and k at respective measuring points.
Figure 9B:
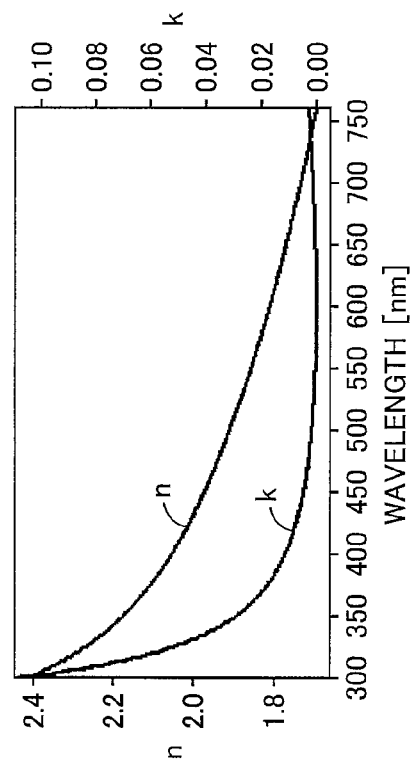

Next, description will be given to results obtained when a sample having different optical constants n and k at respective measuring points is measured (simulated) using optical characteristic measuring apparatus 100. FIGS. 9A to 9D are graphs showing results obtained by measuring a sample having different optical constants n and k at respective measuring points. FIG. 9A shows refractive indexes n at five measuring points in a sample 7. FIG. 9B shows extinction coefficients k at the five measuring points in sample 7. In the graph of refractive indexes n, the horizontal axis indicates a wavelength and the vertical axis indicates a refractive index. In the graph of extinction coefficients k, the horizontal axis indicates a wavelength and the vertical axis indicates an extinction coefficient. Sample 7 is obtained by forming an ITO thin film on a glass substrate. As shown in FIGS. 9A and 9B, in spite of the same ITO thin film of the same sample 7, optical constants n and k are different at the respective measuring points.

Figure 9C:
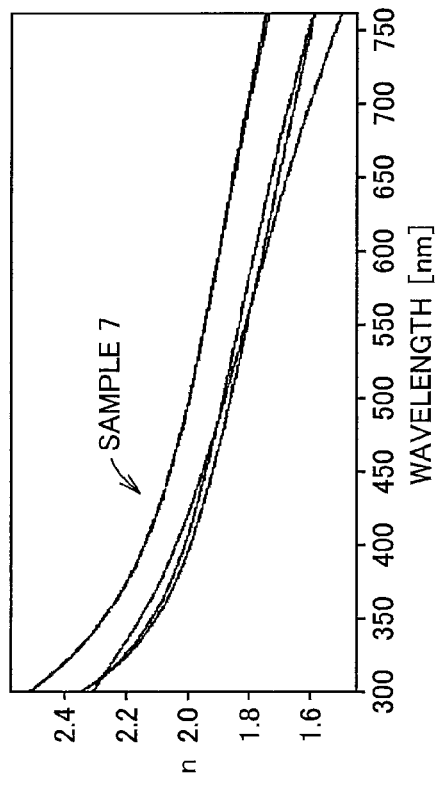
Figure 9D:
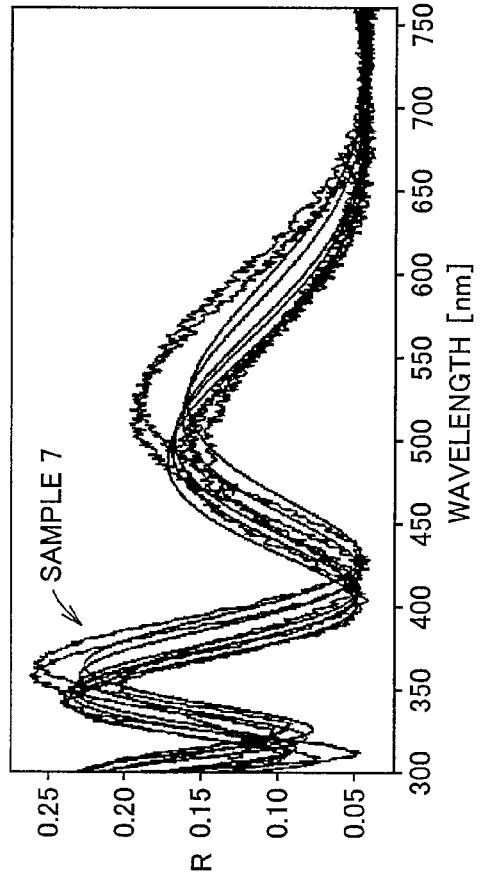

FIGS. 9C and 9D show results obtained by measuring sample 7 using optical characteristic measuring apparatus 100. FIG. 9C shows reflectance spectra at the five measuring points in sample 7. FIG. 9D shows optical constants n and k of the ITO thin film at the five measuring points in sample 7. In the graph of the reflectance spectra, the horizontal axis indicates a wavelength and the vertical axis indicates a reflectance. In the graph of optical constants n and k of the ITO thin film, the horizontal axis indicates a wavelength, and the vertical axis on the left indicates a refractive index and the vertical axis on the right indicates an extinction coefficient.

Even when sample 7 is measured using optical characteristic measuring apparatus 100, optical constants n and k of the ITO thin film can be obtained as the only values as shown in FIG. 9D. However, when fitting is performed between a waveform obtained by substituting obtained optical constants n and k into the film model equations and a waveform of the reflectance spectrum obtained by detector 40 (FIG. 1), both waveforms do not fit each other as shown in FIG. 9C. Therefore, it can be seen that optical constants n and k of the ITO thin film of sample 7 are different at the respective measuring points.

Next, description will be given to results obtained when a sample having a metal thin film formed thereon, of which measurement was difficult using the conventional optical characteristic measuring apparatus, is measured (simulated) using optical characteristic measuring apparatus 100.

Figure 10A:
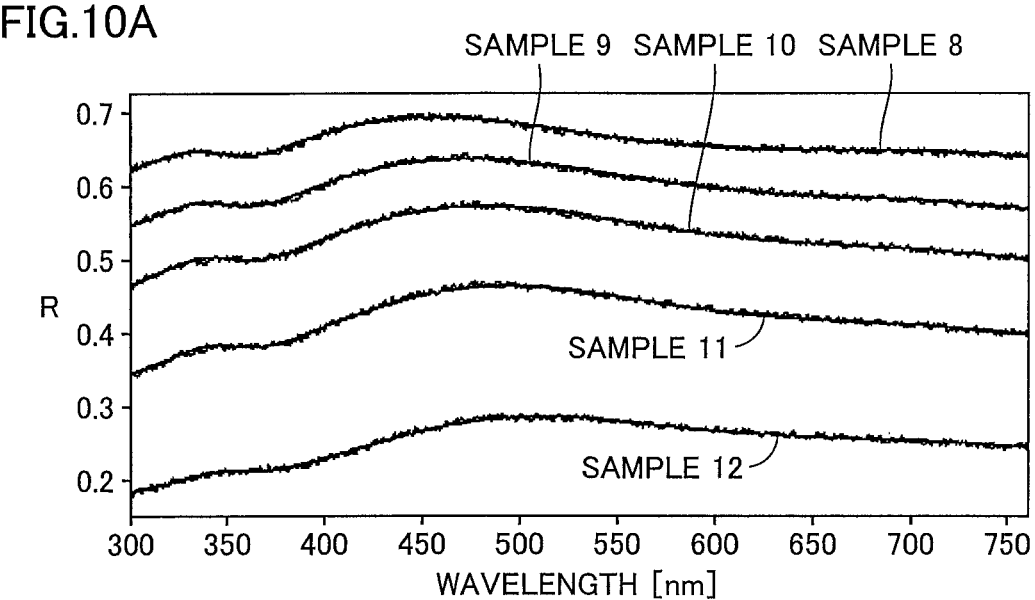
FIGS. 10A and 10B are graphs showing results obtained by measuring samples having a metal thin film formed thereon, using the optical characteristic measuring apparatus according to the first embodiment of the present invention.
Figure 10B:
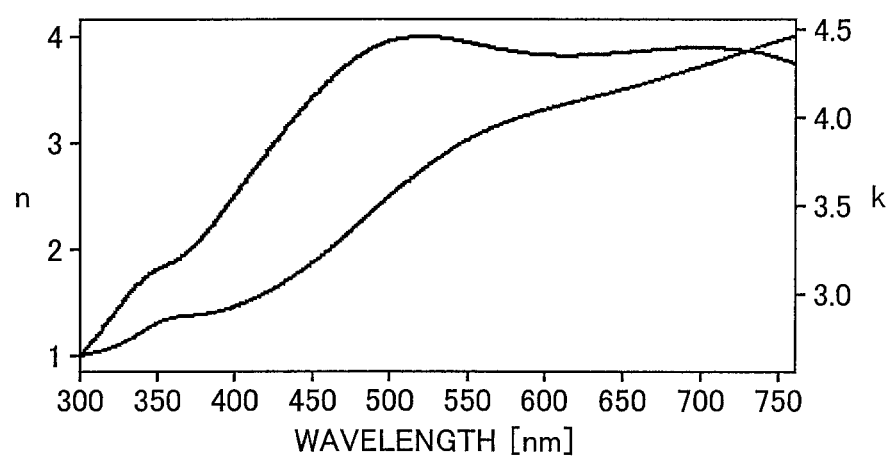

FIGS. 10A and 10B are graphs showing results obtained by measuring samples having a metal thin film formed thereon, using optical characteristic measuring apparatus 100 according to the first embodiment of the present invention. FIG. 10A shows a graph of reflectance spectra of a sample 8 to a sample 12. FIG. 10B shows a graph of optical constants n and k of the metal thin films of sample 8 to sample 12. In the graph of the reflectance spectra, the horizontal axis indicates a wavelength and the vertical axis indicates a reflectance. In the graph of optical constants n and k of the metal thin films, the horizontal axis indicates a wavelength, and the vertical axis on the left indicates a refractive index and the vertical axis on the right indicates an extinction coefficient. Sample 8 to sample 12 are obtained by forming Cr thin films of different film thicknesses on quartz substrates, respectively.

As shown in FIG. 10B, optical constants n and k remain unchanged and remain at the same value in sample 8 to sample 12, and thus, optical constants n and k of the Cr thin film can be obtained as the only values. The film thickness of the Cr thin film of sample 8 is calculated as 32.0 nm. The film thickness of the Cr thin film of sample 9 is calculated as 20.7 nm. The film thickness of the Cr thin film of sample 10 is calculated as 15.5 nm. The film thickness of the Cr thin film of sample 11 is calculated as 10.3 nm. The film thickness of the Cr thin film of sample 12 is calculated as 5.2 nm.

As described above, in optical characteristic measuring apparatus 100 according to the first embodiment of the present invention, analyzing unit 502 solves the plurality of generated film model equations, and performs calculation in accordance with the non-linear least square method on the assumption that optical constants n and k included in the plurality of film model equations are identical, and obtains film thickness d and optical constants n and k of the film. Furthermore, in optical characteristic measuring apparatus 100, fitting unit 503 performs fitting between the waveform obtained by substituting obtained film thickness d and optical constants n and k of the film into the film model equations and the waveform of the spectrum obtained by detector 40, thereby determining that optical constants n and k included in the plurality of film model equations are identical and that obtained film thickness d and optical constants n and k of the film are correct values. Therefore, optical characteristic measuring apparatus 100 can obtain, as the only values, optical constants n and k of the film formed on the substrate, based on the obtained spectrum. In addition, in optical characteristic measuring apparatus 100 according to the first embodiment of the present invention, fitting unit 503 verifies film thickness d and optical constants n and k of the film obtained by analyzing unit 502. Therefore, film thickness d and optical constants n and k of the film can be measured with higher accuracy.

Equation (13) above is a determinant when the rear surface reflection coefficient contribution ratio is omitted ($\gamma=1$) in the sample having one layer of thin film formed on the substrate.

In optical characteristic measuring apparatus 100 according to the present invention, however, the determinant is not limited to equation (13), and may be a determinant when the rear surface reflection coefficient contribution ratio is taken into consideration in a sample having multiple layers of thin films formed on a substrate. Specifically, a determinant expressed by equation (15) below is used. In equation (15) below, a parameter taking the multiple layers of thin films and the rear surface reflection coefficient contribution ratio into consideration is added as appropriate to the latter term (e.g., the term next to the term partially differentiating $f_{11}$ by $d_m$, lower part of $\Delta d_m$).

$$\begin{bmatrix} \Delta Y_{11} \\ \vdots \\ \Delta Y_{1n} \\ \vdots \\ \Delta Y_{m1} \\ \vdots \\ \Delta Y_{mn} \end{bmatrix} = \begin{bmatrix} \frac{\partial f_{11}}{\partial C_1} & \frac{\partial f_{11}}{\partial C_2} & \frac{\partial f_{11}}{\partial C_3} & \frac{\partial f_{11}}{\partial d_1} & \frac{\partial f_{11}}{\partial d_2} & \cdots & \frac{\partial f_{11}}{\partial d_m} & \cdots \\ \vdots & \vdots & \vdots & \vdots & \vdots & \ddots & \vdots & \cdots \\ \frac{\partial f_{1n}}{\partial C_1} & \frac{\partial f_{1n}}{\partial C_2} & \frac{\partial f_{1n}}{\partial C_3} & \frac{\partial f_{1n}}{\partial d_1} & \frac{\partial f_{1n}}{\partial d_2} & \cdots & \frac{\partial f_{1n}}{\partial d_m} & \cdots \\ \vdots & \vdots & \vdots & \vdots & \vdots & \ddots & \vdots & \cdots \\ \frac{\partial f_{m1}}{\partial C_1} & \frac{\partial f_{m1}}{\partial C_2} & \frac{\partial f_{m1}}{\partial C_3} & \frac{\partial f_{m1}}{\partial d_1} & \frac{\partial f_{m1}}{\partial d_2} & \cdots & \frac{\partial f_{m1}}{\partial d_m} & \cdots \\ \vdots & \vdots & \vdots & \vdots & \vdots & \ddots & \vdots & \cdots \\ \frac{\partial f_{mn}}{\partial C_1} & \frac{\partial f_{mn}}{\partial C_2} & \frac{\partial f_{mn}}{\partial C_3} & \frac{\partial f_{mn}}{\partial d_1} & \frac{\partial f_{mn}}{\partial d_2} & \cdots & \frac{\partial f_{mn}}{\partial d_m} & \cdots \end{bmatrix} \begin{bmatrix} \Delta C_1 \\ \Delta C_2 \\ \Delta C_3 \\ \Delta d_1 \\ \Delta d_2 \\ \vdots \\ \Delta d_m \\ \vdots \\ \vdots \end{bmatrix}$$

equation (15)

$$Yc_{xy} = f_{xy}(\phi, \lambda_y, N_{x0}, N_{x1}, d_{x1}, \ldots, N_{xi}, d_{xi}, \gamma)$$
$$(x = 1 \sim m, y = 1 \sim n)$$

Figure 11:
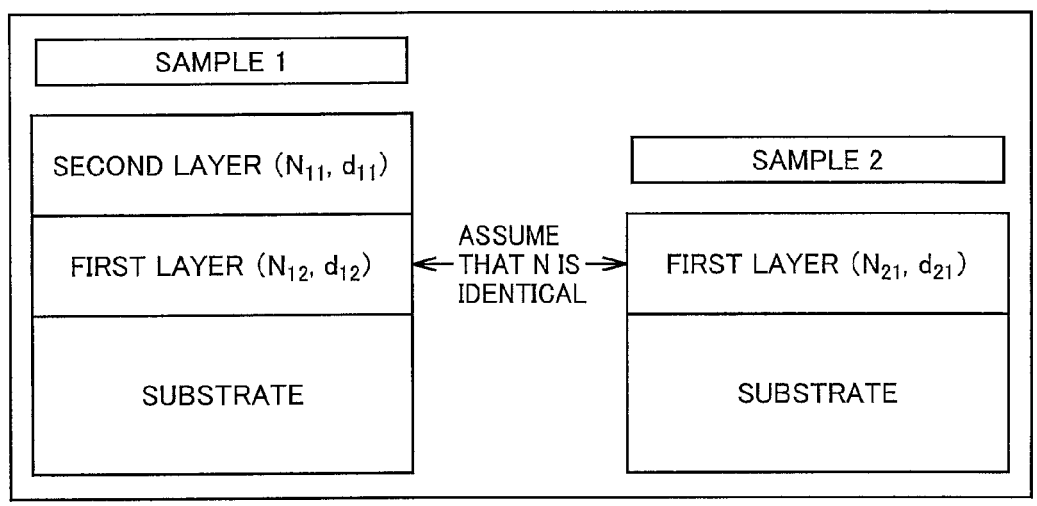
FIG. 11 is a schematic view showing a layer configuration of the sample measured by the optical characteristic measuring apparatus.

In addition, all of the samples measured by optical characteristic measuring apparatus 100 are not always have to have the same layer configuration, and the samples may have different layer configurations. FIG. 11 is a schematic view showing a layer configuration of the sample measured by optical characteristic measuring apparatus 100. Sample 1 shown in FIG. 11 has such a layer configuration that a first layer and a second layer are stacked on a substrate. Sample 2 has such a layer configuration that a first layer is stacked on a substrate. The first layer of sample 1 has a complex refractive index $N_{12}$ and a film thickness $d_{12}$, and the second layer of sample 1 has a complex refractive index $N_{11}$ and a film thickness $d_{21}$. The first layer of sample 2 has a complex refractive index $N_{21}$ and a film thickness $d_{21}$. Optical characteristic measuring apparatus 100 conducts measurement on the assumption that complex refractive index N of the first layer of sample 1 and complex refractive index N of the first layer of sample 2 are identical ($N_{12}=N_{21}$).

Second Embodiment

Figure 12:
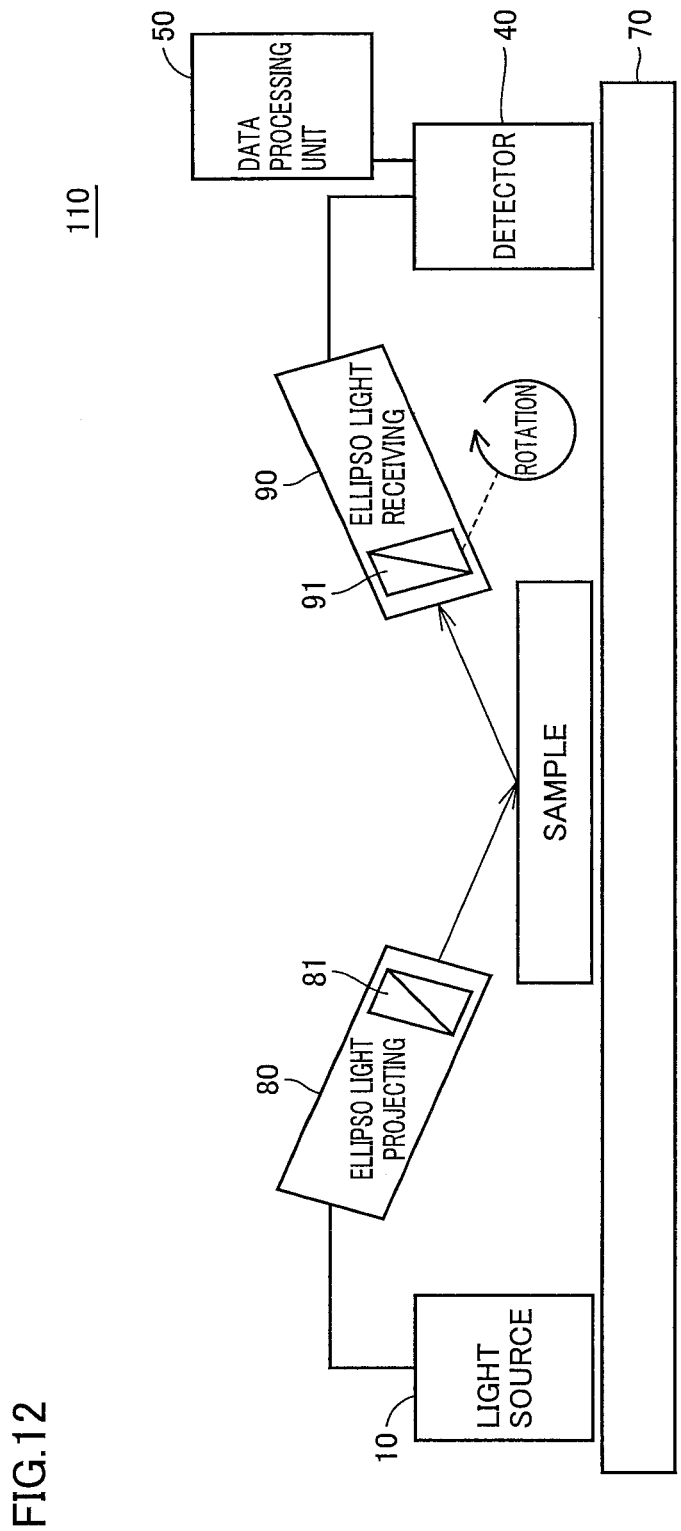
FIG. 12 is a schematic configuration diagram of an optical characteristic measuring apparatus according to a second embodiment of the present invention.

<Apparatus Configuration>
FIG. 12 is a schematic configuration diagram of an optical characteristic measuring apparatus 110 according to a second embodiment of the present invention.

Optical characteristic measuring apparatus 110 according to the second embodiment is a spectroscopic ellipsometer, where a film thickness of each layer can be measured by irradiating a sample with light (incident light) including at least a prescribed ultraviolet wavelength range, and measuring a spectroscopic ellipsoparameter in a particular wavelength of reflected light generated as a result of reflection of this incident light from the sample.

Specifically, in optical characteristic measuring apparatus 110, the sample is irradiated with light, and based on a wavelength distribution characteristic (hereinafter also referred to as "spectrum") of polarized reflection light reflected from the sample, a film thickness and optical constants (refractive index n, extinction coefficient k) of a film constituting the sample can be measured.

Referring to FIG. 12, optical characteristic measuring apparatus 110 includes measuring light source 10, an ellipso light projecting unit 80, an ellipso light receiving unit 90, detector 40, data processing unit 50, and stage 70. The sample is set on stage 70.

Measuring light source 10 generates light having a wavelength range including a prescribed ultraviolet wavelength range (e.g., 185 nm to 400 nm). Measuring light source 10 is typically a white light source such as a xenon lamp (Xe lamp) or a deuterium lamp (D2 lamp) that can generate a wavelength ranging from the ultraviolet region to the visible region. The light generated by measuring light source 10 is guided through an optical fiber and the like to ellipso light projecting unit 80.

Ellipso light projecting unit 80 includes a polarizing prism 81. Polarizing prism 81 is a polarizer and converts the light generated by measuring light source 10 to polarized light. The sample is irradiated with the converted polarized light. Ellipso light projecting unit 80 may be provided with a ¼λ wavelength plate and convert, to circular polarized light, the light with which the sample is irradiated.

Ellipso light receiving unit 90 includes a polarizing prism 91. Polarizing prism 91 is an analyzer and converts the reflected light generated as a result of reflection from the sample to linear polarized light. This reflected light after conversion to the linear polarized light is guided through the optical fiber and the like to detector 40. Polarizing prism 91 is coupled to a rotary motor (not shown) and generates the linear polarized light in the polarization direction corresponding to the rotational position of this rotary motor.

Since detector 40 and data processing unit 50 have substantially the same configurations as those of detector 40 and data processing unit 50 in the first embodiment, detailed description thereof will not be repeated. In addition, since data processing unit 50 has the same structure as the calculation processing structure described in the first embodiment and executes similar calculation processing, detailed description thereof will not be repeated.

<Measuring Method>

Next, an optical characteristic measuring method according to the second embodiment of the present invention will be described with reference to a flowchart.

Figure 13:
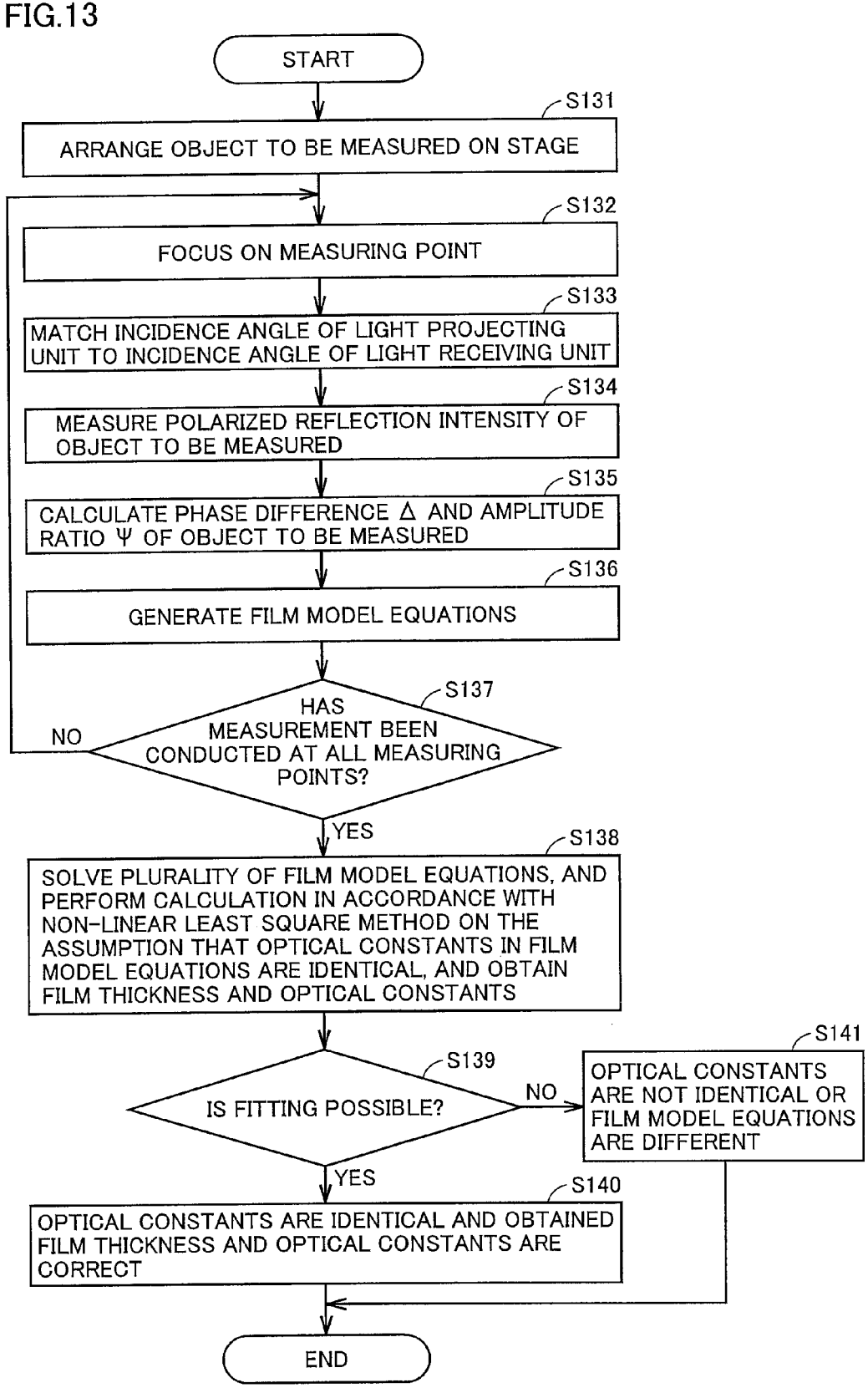
FIG. 13 is a flowchart showing a process procedure of an optical characteristic measuring method according to the second embodiment of the present invention.

FIG. 13 is a flowchart showing a process procedure of the optical characteristic measuring method according to the second embodiment of the present invention.

Referring to FIG. 13, the user first arranges an object to be measured (sample) on stage 70 (FIG. 12) (step S131).

Then, the user moves ellipso light projecting unit 80 to focus on a measuring point of the sample such that the measuring point is irradiated with light provided from ellipso light projecting unit 80 (step S132). Furthermore, the user matches an incidence angle of ellipso light projecting unit 80 to an incidence angle of ellipso light receiving unit 90 such that the light provided from ellipso light projecting unit 80 can be reflected from the measuring point of the sample and received by ellipso light receiving unit 90 (step S133).

When the user provides the measurement start command after focusing on the measuring point and matching the incidence angle of ellipso light projecting unit 80 to the incidence angle of ellipso light receiving unit 90, generation of measuring light from measuring light source 10 (FIG. 12) starts. Detector 40 receives the polarized reflection light from the sample and outputs a reflection intensity spectrum based on this polarized reflection light to data processing unit 50 (polarized reflection intensity measurement) (step S134). Then, CPU 200 in data processing unit 50 temporarily stores the reflection intensity spectrum detected by detector 40 in memory unit 212 and the like, and thereafter, calculates phase difference Δ and amplitude ratio Ψ of the sample based on the reflection intensity spectrum (step S135).

CPU 200 generates film model equations including at least calculated phase difference Δ and amplitude ratio Ψ of the sample as well as the film thickness and the optical constants of the film (step S136). Then, CPU 200 determines whether or not measurement has been conducted at all measuring points (step S137). If CPU 200 determines that measurement has not yet been conducted at all measuring points (NO in step S137), the user moves ellipso light projecting unit 80 to focus on the next measuring point of the sample such that the next measuring point is irradiated with the light provided from ellipso light projecting unit 80 (step S132).

If CPU 200 determines that measurement has been conducted at all measuring points (YES in step S137), the process proceeds to step S138. CPU 200 solves the plurality of film model equations, and performs calculation in accordance with the non-linear least square method on the assumption that the optical constants included in the plurality of film model equations are identical, and obtains film thickness $d_i$ and optical constants n and k of the film (step S138).

Furthermore, CPU 200 performs fitting between a waveform obtained by substituting obtained film thickness $d_i$ and optical constants n and k of the film into the film model equations and a waveform of the spectrum obtained by detector 40, and determines whether or not fitting is possible (step S139). If CPU 200 determines that fitting is possible (YES in step S139), CPU 200 determines that optical constants n and k included in the plurality of film model equations are identical and that obtained film thickness $d_i$ and optical constants n and k of the film are correct (step S140). If CPU 200 determines that fitting is impossible (NO in step S139), CPU 200 determines that optical constants n and k included in the plurality of film model equations are not identical or that the generated film model equations are different (step S141).

As described above, even in optical characteristic measuring apparatus 110 according to the second embodiment of the present invention, the film model equations including at least calculated phase difference Δ and amplitude ratio Ψ of the sample as well as the film thickness and the optical constants of the film are generated and processing similar to that in the first embodiment is executed. Therefore, optical constants n and k of the film formed on the substrate can be obtained as the only values based on the obtained spectrum.

As shown in FIGS. 7A to 7C, in the conventional optical characteristic measuring apparatus, when optical constants n and k changed depending on samples, it could not be determined whether optical constants n and k of the respective samples were actually different from one another or it was caused by errors in measurement factors.

In optical characteristic measuring apparatus 100 and 110 according to the present invention, however, fitting is performed between the waveform obtained by substituting obtained film thickness $d_i$ and optical constants n and k of the film into the film model equations and the waveform of the spectrum obtained by detector 40, and thereby it can be verified whether or not optical constants n and k of the respective samples are actually different from one another. In other words, in optical characteristic measuring apparatus 100 and 110, when fitting is possible (when residual ΔY is small), the only optical constants n and k are obtained on the assumption that optical constants n and k of the respective samples are identical. When fitting is impossible (when residual ΔY is large), it can be determined that optical constants n and k of the respective samples are actually different from one another.

Figure 14:
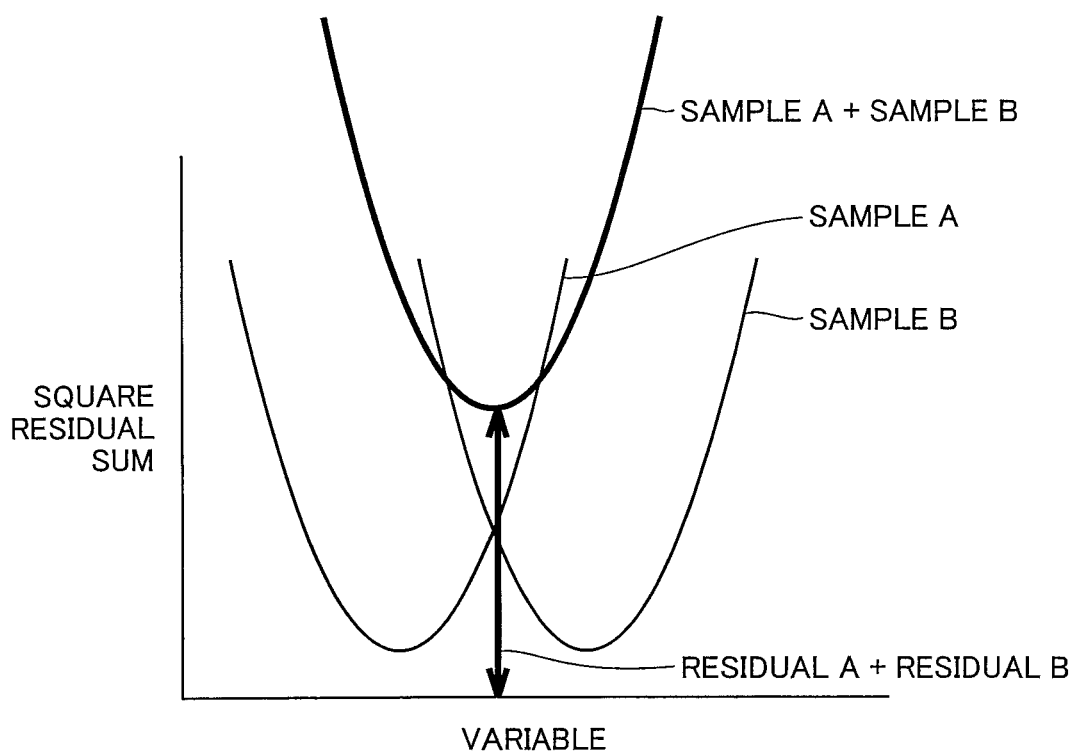
FIG. 14 is a schematic view showing a relationship between a residual $\Delta Y$ evaluated in the optical characteristic measuring apparatus according to the present invention and residuals of respective samples.

Residual ΔY evaluated in optical characteristic measuring apparatus 100 and 110 is a sum of residuals of the respective samples. FIG. 14 is a schematic view showing a relationship between residual ΔY evaluated in optical characteristic measuring apparatus 100 and 110 according to the present invention and the residuals of the respective samples. In FIG. 14, the horizontal axis indicates a variable and the vertical axis indicates a square residual sum, and FIG. 14 shows changes in the residuals of a sample A, a sample B, and sample A+sample B. Residual ΔY evaluated in optical characteristic measuring apparatus 100 and 110 is the residual of sample A+sample B, and is a sum of residual A of sample A and residual B of sample B (residual A+residual B), which is indicated by an arrow. The magnitude of a change in optical constants n and k can also be quantified based on a ratio of the magnitude of the residuals of the respective samples.

In the manufacturing line of semiconductor devices and the like, it is necessary to predetermine optical constants n and k as certain values in order to control a value of the film thickness by in-line measurement, fully-automatic measurement or the like. In optical characteristic measuring apparatus 100 and 110 according to the present invention, there are obtained optical constants n and k when a sum of residuals of a plurality of samples is small. Therefore, even when samples or measuring points having different optical constants n and k are measured, an intermediate value of the different optical constants n and k can be obtained. Therefore, optical constants n and k measured by optical characteristic measuring apparatus 100 and 110 can be used as provisional optical constants for controlling a value of the film thickness by in-line measurement, fully-automatic measurement or the like.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An optical characteristic measuring apparatus, comprising:
   a light source irradiating an object to be measured, which has at least one layer of film formed on a substrate, with measuring light having a prescribed wavelength range;
   a spectrometric measuring unit obtaining a wavelength distribution characteristic of reflection intensity or transmission intensity based on light reflected from said object to be measured or light that has passed through said object to be measured;
   a modeling unit obtaining a plurality of said wavelength distribution characteristics from said film of a same material, and generating a plurality of film model equations including at least a parameter calculated from each of said obtained wavelength distribution characteristics as well as a film thickness and optical constants of said film;
   an analyzing unit solving said plurality of film model equations generated by said modeling unit, and performing prescribed calculation on the assumption that said optical constants included in said plurality of film model equations is identical, and obtaining said film thickness and said optical constants of said film; and
   a fitting unit performing fitting between a waveform obtained by substituting said film thickness and said optical constants of said film obtained by said analyzing unit into said film model equations and a waveform of said wavelength distribution characteristic obtained by said spectrometric measuring unit, thereby determining that said optical constants included in said plurality of film model equations is identical and that said film thickness and said optical constants of said film obtained by said analyzing unit are correct values.

2. The optical characteristic measuring apparatus according to claim 1, wherein
   said analyzing unit uses a non-linear least square method for said prescribed calculation.

3. The optical characteristic measuring apparatus according to claim 1, wherein
   said parameter calculated from said wavelength distribution characteristic is a reflectance or a transmittance of said film.

4. The optical characteristic measuring apparatus according to claim 1, wherein
   said spectrometric measuring unit obtains said wavelength distribution characteristic of polarized reflection intensity based on the light reflected from said object to be measured, and
   said parameter calculated from said wavelength distribution characteristic is a phase difference $\Delta$ and an amplitude ratio $\Psi$.

5. The optical characteristic measuring apparatus according to claim 1, wherein
   said modeling unit generates said film model equations further including a rear surface reflection coefficient contribution ratio of said film.

6. An optical characteristic measuring method, comprising the steps of:
   irradiating an object to be measured, which has at least one layer of film formed on a substrate, with measuring light having a prescribed wavelength range;
   obtaining a plurality of wavelength distribution characteristics of reflection intensity or transmission intensity from said film of a same material, based on light reflected from said object to be measured or light that has passed through said object to be measured;
   generating a plurality of film model equations including a parameter calculated from each of said obtained wavelength distribution characteristics as well as a film thickness and optical constants of said film;
   solving said plurality of generated film model equations, and performing prescribed calculation on the assumption that said optical constants included in said plurality of film model equations is identical, and obtaining said film thickness and said optical constants of said film; and
   performing fitting between a waveform obtained by substituting said obtained film thickness and said obtained optical constants of said film into said film model equations and a waveform of said obtained wavelength distribution characteristic, thereby determining that said optical constants included in said plurality of film model equations is identical and that said obtained film thickness and said obtained optical constants of said film are correct values.

* * * * *